(12) United States Patent
Martens et al.

(10) Patent No.: US 8,153,067 B2
(45) Date of Patent: Apr. 10, 2012

(54) CIRCUIT WITH AT LEAST ONE CATALYTIC MEASURING ELEMENT

(75) Inventors: Matthias Martens, Gross Schenkenberg (DE); Mladen Schlichte, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 1866 days.

(21) Appl. No.: 11/370,528

(22) Filed: Mar. 8, 2006

(65) Prior Publication Data

US 2006/0257289 A1 Nov. 16, 2006

(30) Foreign Application Priority Data

May 14, 2005 (DE) .................... 10 2005 022 471

(51) Int. Cl.
*G01N 31/12* (2006.01)
*G01N 27/16* (2006.01)

(52) U.S. Cl. ................. 422/94; 422/95; 422/96; 422/97

(58) Field of Classification Search ..................... 422/94
See application file for complete search history.

(56) References Cited

FOREIGN PATENT DOCUMENTS

WO    WO 9427139 A1 * 11/1994
* cited by examiner

*Primary Examiner* — Jill Warden
*Assistant Examiner* — Bryan Kilpatrick
(74) *Attorney, Agent, or Firm* — McGlew and Tuttle, P.C.

(57) ABSTRACT

A circuit with at least one catalytic measuring element (1), in which the at least one catalytic measuring element (1) is connected to a supply voltage (5) without a protective resistor and without a thermal safety device arranged upstream. The circuit makes it possible to develop gas-measuring devices with catalytic measuring elements that are characterized by an especially low power consumption.

12 Claims, 3 Drawing Sheets

CIRCUIT WITH AT LEAST ONE CATALYTIC MEASURING ELEMENT

CROSS REFERENCE TO RELATED APPLICATIONS

This application claims the benefit of priority under 35 U.S.C. §119 of German Patent Application DE 10 2005 022 471.7 filed May 14, 2005, the entire contents of which are incorporated herein by reference.

FIELD OF THE INVENTION

The present invention pertains to a circuit with at least one catalytic measuring element.

BACKGROUND OF THE INVENTION

Devices that operate with catalytic measuring elements to perform gas measurements have been used in gas measuring engineering applications. In particular, pellistors are widely used for in gas measuring engineering applications.

General conditions must be taken into account when such measuring elements are used. These conditions arise from the fact that the electric properties of such catalytic measuring elements may change during the measurement. Also, they are possibly used in the presence of an explosion hazard.

The pellistors are considered to be semiconductor elements especially in conventional circuits with pellistors. Since the resistance of these pellistors may change substantially as a function of the temperature, protective resistors and thermal safety devices are usually used to limit the maximum power of the pellistor and at the same time to limit the maximum current to values at which ignition by spark is ruled out in an environment with explosion hazard.

The drawback of such a circuit is, however, that both a protective resistor and a thermal safety device represent separate users and they consume electric power. This represents a considerable drawback, especially in case of portable devices that are battery-operated. The use time is substantially reduced in this manner. Consequently, more energy must be made available than would be necessary for the operation of the pellistor alone. The energy storage means necessary for this, for example, batteries, increase the weight of such devices in a disadvantageous manner.

SUMMARY OF THE INVENTION

The object of the present invention is to provide a circuit with catalytic measuring elements, which can be operated with an especially low energy consumption.

According to the invention, a circuit is provided with at least one catalytic measuring element. The at least one catalytic measuring element is connected to a supply voltage without a protective resistor and without a thermal safety device arranged upstream.

The present invention is based on the fact that it is possible to dimension a catalytic measuring element such that even though its resistance is a temperature-dependent variable, it does change within limits which ensure a sufficient limitation of the current at any time and thus make it possible to effectively prevent an ignition by spark in an environment with explosion hazard. Furthermore, the catalytic measuring element is to be dimensioned such that it can assume the function of a thermal safety device that limits the power fed to the measuring element. The catalytic measuring element thus also assumes at the same time the protective function for a possibly series-connected electronic unit, for example, a power electronic unit, via which the current flow necessary for the measuring operation through the catalytic measuring element is embodied.

It is thus possible according to the present invention to do away with a protective resistor or a thermal safety device arranged upstream. The present invention can be advantageously used in circuits that contain a plurality of, but at least two catalytic measuring elements. In particular, circuits that contain at least one pellistor can be set up in the manner according to the present invention. At least one pellistor is advantageously dimensioned here such that it limits the current at a point in time to a value that prevents ignition by a spark in an environment with explosion hazard. This function is ensured according to the present invention regardless of the operating temperature at which the pellistor is used for measurements.

The same pellistor can advantageously be dimensioned such that it acts as a thermal safety device to limit the power that is fed to the pellistor. In particular, pellistors with a wire coil made of platinum or a platinum alloy and a catalytic bead made of $\gamma$-aluminum oxide or a mixture of $\gamma$-aluminum oxide and zirconium oxide with catalysts from precious metal particles can be dimensioned and used according to the present invention.

Advantageous materials of which the precious metal particles of the catalyst consist are platinum, rhodium, palladium or combinations of these precious metals. The circuit according to the present invention can also be used advantageously if two pellistors are used for the measurement.

The present invention will be explained in greater detail on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
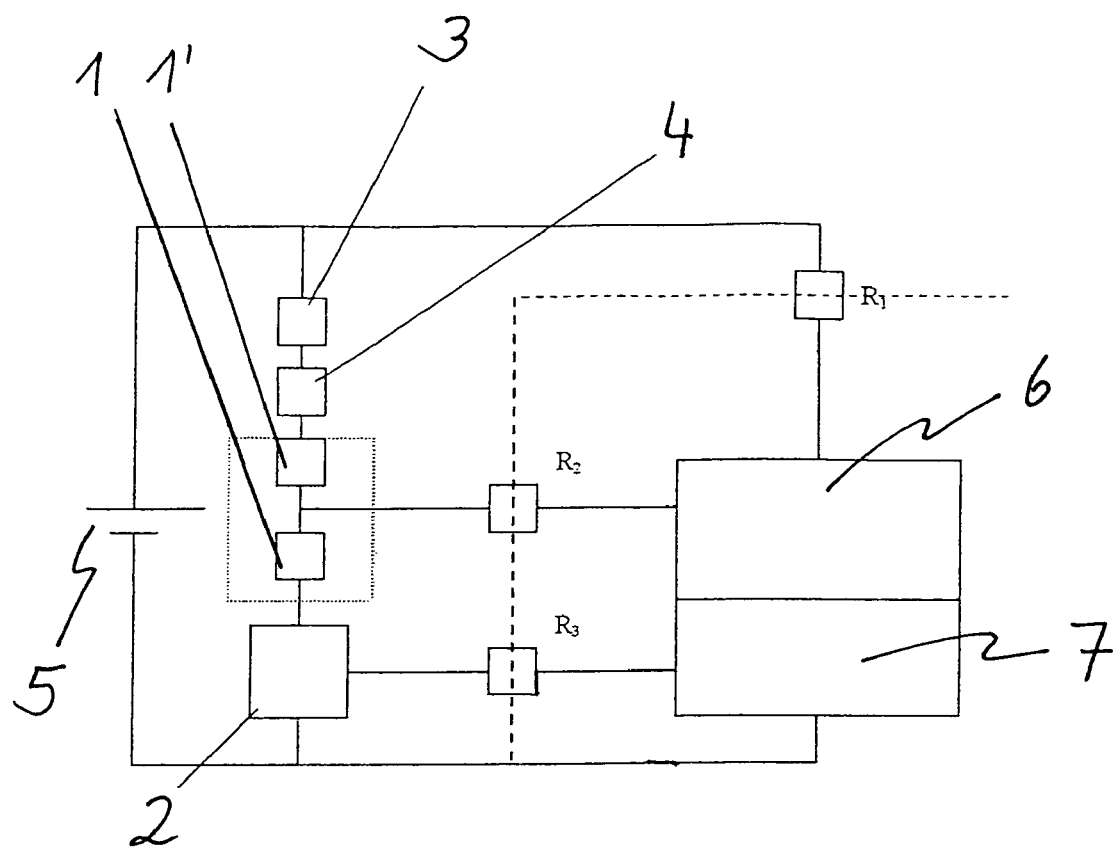
FIG. 1 is a circuit diagram view showing a circuit with two pellistors according to the state of the art.

Referring to the drawings in particular, FIG. 1 shows a circuit with two pellistors as catalytic measuring elements 1, 1'. These are connected in series with a power electronic assembly unit 2, a protective resistor 3 and a thermal safety device 4 as a protection for the protective resistor 3 and all series-connected elements. The output voltage of a power source 5 is applied to this series-connected arrangement. An electronic assembly unit with an evaluating electronic unit 6 is used to evaluate the measured signals, which are sent by the arrangement of pellistors. An assembly unit with actuating electronic unit 7 is used to actuate the power electronic assembly unit 2. The evaluating electronic unit and the actuating electronic unit are likewise supplied by the power source 5, but are connected to the power source 5, the output signal of the pellistors and the power electronic assembly unit 2 via high-ohmic resistors R1, R2, R3.

Figure 2:
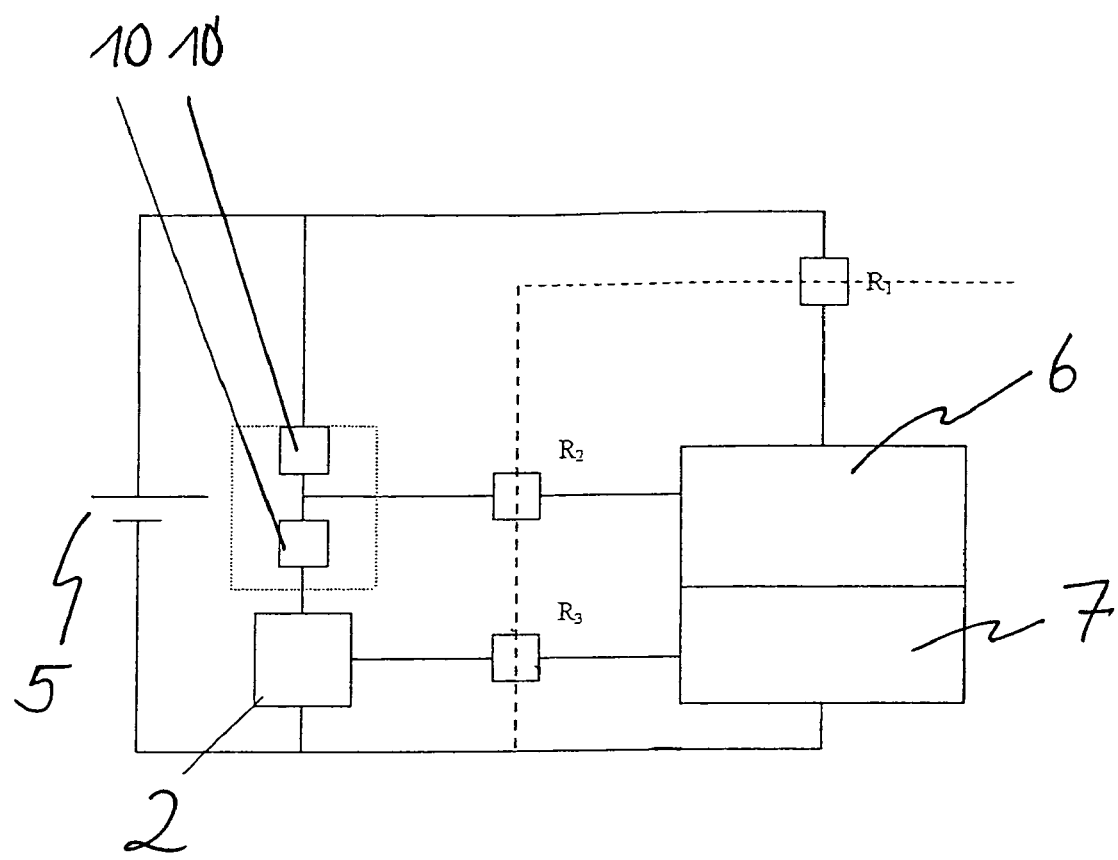
FIG. 2 is a circuit designed according to the present invention with two pellistors dimensioned according to the present invention without a protective resistor and without a thermal safety device.

FIG. 2 shows a circuit designed according to the present invention with two pellistors dimensioned according to the present invention without a protective resistor and without a thermal safety device. The series-connected arrangement, which is supplied with the output voltage of the power source 5, contains only an arrangement of two pellistors as catalytic measuring elements 10, 10' and a power electronic assembly unit 2, which is necessary for the operation of the pellistors. An-assembly unit with an actuating electronic unit 7 and an assembly unit with an evaluating electronic unit 6, which are again uncoupled from the rest of the circuit by high-ohmic resistors R1, R2, R3, are likewise present again.

The pellistors 10, 10' are designed according to the present invention such that they act, on the one hand, as a thermal safety device to limit the power that can be fed to the pellistors and have, on the other hand, a minimum resistance that prevents ignition by sparks at any time. At the same time, they assume the protective function for the series-connected power electronic assembly unit 2.

Figure 3:
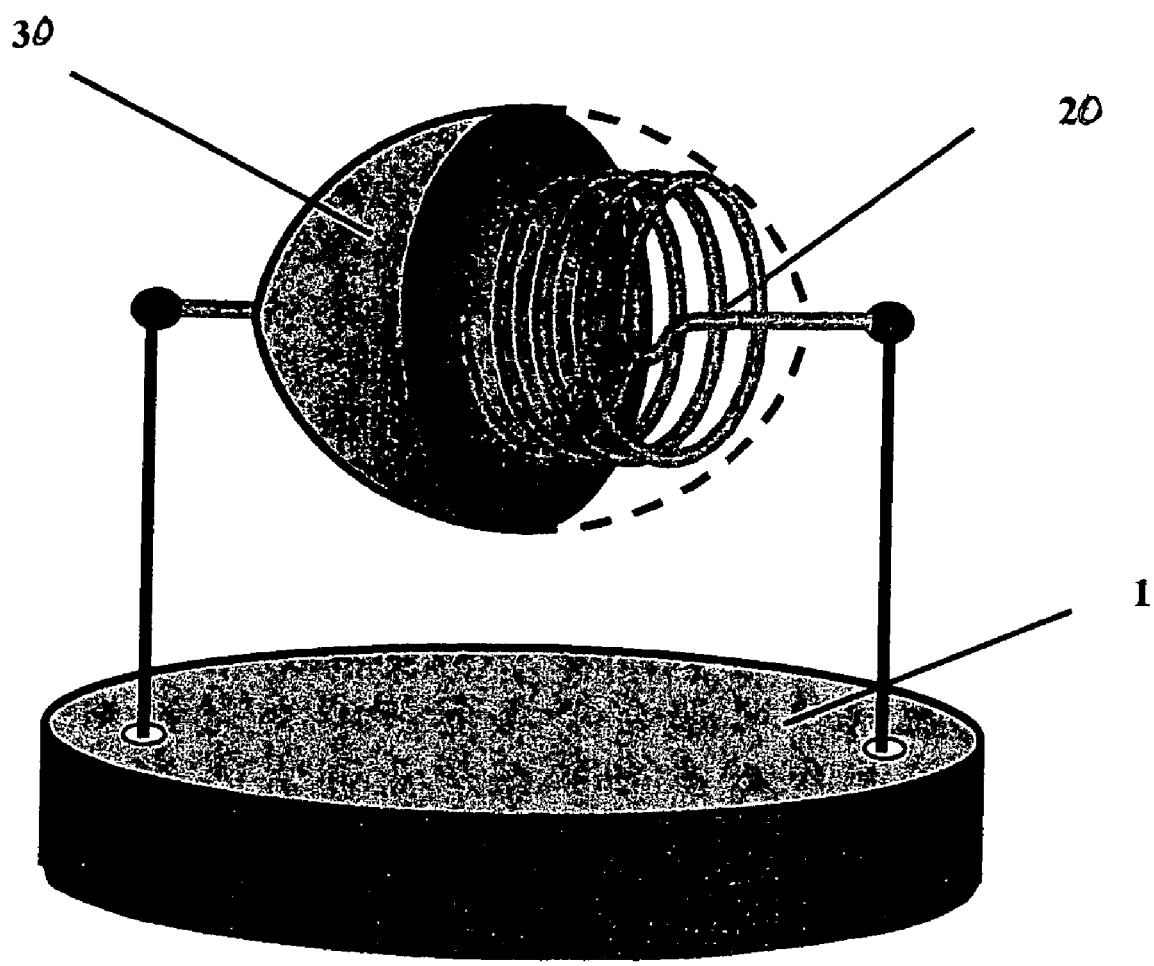
FIG. 3 is a schematic perspective view showing the design of each pellistor of the circuit of FIG. 2 with a catalytic bead with carrier material and catalyst shown in section.

It is possible to do away with a protective resistor and a thermal safety device for the first time because of this functionality. This arrangement according to the present invention is made possible by the specification of the pellistors 10, 10'. As shown in FIG. 3, every individual pellistor 10, 10' contains a wire coil 20 consisting (or consisting essentially) of a platinum alloy with a wire diameter of 0.01 mm to 0.08 mm. The wire coil 20 is connected by mounting pins to the circuit board 1. The material of the catalytic bead 30 consists either of γ-aluminum oxide or a mixture of γ-aluminum oxide and zirconium oxide, using catalysts from precious metal particles such as platinum, rhodium, palladium or combinations of these precious metals. The individual pellistor 10, 10' is dimensioned such that its resistance is in a range between 3 and 25 Ohm at an applied voltage of 500 mV to 2,500 mV. The actual voltage does not drop below nor exceed this range even at different operating temperatures, which may become necessary for the measurement of the gases to be detected. It can thus be ensured that ignition by sparks is effectively prevented from occurring in any state of operation.

Based on the circuit according to the present invention, the pellistors necessary for the measurement form the only users themselves that consume energy to an appreciable extent. Due to this circuit, portable gas-measuring devices with a substantially lower energy consumption can be designed, which means, in return, a substantially longer use time at a given weight.

While specific embodiments of the invention have been shown and described in detail to illustrate the application of the principles of the invention, it will be understood that the invention may be embodied otherwise without departing from such principles.

What is claimed is:

1. A circuit comprising:
    a supply voltage; and
    a catalytic measuring element connected to said supply voltage without a protective resistor and without a thermal safety device arranged upstream, said catalytic measuring element comprising a pellistor dimensioned to have a temperature-dependent variable resistance that limits the current at any point in time to a value that prevents ignition by sparks in an environment with explosion hazard and does not change beyond limits to ensure a sufficient limitation of the current at any time whereby an ignition by spark is effectively prevented in an environment with explosion hazard and said pellistor is dimensioned to act as a thermal safety device to limit the output that can be fed to said pellistor and wherein said pellistor contains a wire coil consisting of platinum or a platinum alloy with a wire diameter of 0.01 mm to 0.08 mm and a catalytic bead consisting of γ-aluminum oxide or a mixture of γ-aluminum oxide and zirconium oxide with catalysts from precious metal particles and is dimensioned such that its resistance is in the range between 3 Ohm and 25 Ohm at an applied voltage of 500 mV to 2,500 mV.

2. A circuit in accordance with claim 1, further comprising;
    another catalytic measuring element connected to said supply voltage without a protective resistor and without a thermal safety device arranged upstream.

3. A circuit in accordance with claim 1, wherein the catalysts consisting of precious metal particles comprise particles consisting of platinum, rhodium, palladium or combinations of these precious metals.

4. A circuit in accordance with claim 2, wherein said another catalytic measuring element comprises a pellistor.

5. A measuring circuit comprising:
    a supply voltage;
    a catalytic measuring element defining a thermal safety means for limiting power fed to said catalytic measuring element with said catalytic measuring element having a minimum resistance range to ensure a sufficient limitation of the current at any time whereby an ignition by spark is effectively prevented in an environment with explosion hazard and being connected to said supply voltage without a protective resistor and without a thermal safety device connected in the measuring circuit; and
    another catalytic measuring element defining a thermal safety means for limiting power fed to said catalytic measuring element with said catalytic measuring element having a minimum resistance range and being connected to said supply voltage without a protective resistor and without a thermal safety connected in the measuring circuit, wherein:
    said catalytic measuring element comprises a first pellistor and said another catalytic measuring element comprises a second pellistor;
    said first pellistor and said second pellistor are each dimensioned such that each pellistor limits the current at any point in time to a value under a threshold so as to substantially prevent sparks and prevent ignition of explosion hazard material in an environment with each of said first pellistor and said second pellistor comprising a wire coil consisting of platinum or a platinum alloy with a wire diameter of 0.01 mm to 0.08 mm and a catalytic bead consisting of γ-aluminum oxide or a mixture of γ-aluminum oxide and zirconium oxide and with said catalytic measuring element dimensioned such that said catalytic measuring element has a resistance in the range from 3 Ohm to 25 Ohm at an applied voltage of 500 mV to 2,500 mV.

6. A measuring circuit in accordance with claim 5, wherein each of said first pellistor and said second pellistor comprises catalysts from precious metal particles.

7. A measuring circuit in accordance with claim 6, wherein the catalysts consisting of precious metal particles comprise particles consisting of platinum, rhodium, palladium or combinations of these precious metals.

8. A measuring circuit for measurement of the gases in an environment, the measuring circuit comprising:
a supply voltage; and
a circuit branch in parallel to said supply voltage with a first pellistor measuring element connected in parallel with said supply voltage and defining a measuring element with a first thermal safety means for limiting power fed to said first pellistor measuring element with said first pellistor measuring element having a resistance in a range between 3 and 25 Ohm at an applied voltage of 500 mV to 2,500 mV, a voltage of said first pellistor measuring element not dropping below nor exceeding said range even at different operating temperatures, said first pellistor measuring element being connected in said circuit branch to said supply voltage and a second pellistor measuring element connected in parallel with said supply voltage and defining another measuring element with a second thermal safety means for limiting power fed to said second pellistor measuring element with said second pellistor measuring element having a second resistance in said range at an applied voltage of 500 mV to 2,500 mV, said second pellistor measuring element voltage not dropping below nor exceeding said range even at different operating temperatures, said first pellistor measuring element and said second pellistor measuring element being connected in said circuit branch in series without a protective resistor and without a thermal safety device connected in said circuit branch.

9. A measuring circuit in accordance with claim 8, wherein each of said first pellistor measuring element and said second pellistor measuring element comprise a wire coil consisting of platinum or a platinum alloy with a wire diameter of 0.01 mm to 0.08 mm and a catalytic bead consisting of γ-aluminum oxide or a mixture of γ-aluminum oxide and zirconium oxide.

10. A measuring circuit in accordance with claim 9, wherein each of said first pellistor and said second pellistor comprises catalysts from precious metal particles.

11. A measuring circuit in accordance with claim 8, further comprising:
a power electronic assembly unit connected in said circuit branch in series with said first pellistor measuring element and said second pellistor measuring element; and
an evaluating and actuating assembly unit connected to said circuit branch via high ohmic resistors.

12. A measuring circuit in accordance with claim 5, further comprising:
a power electronic assembly unit connected in a circuit branch in series with said first pellistor and said second pellistor, said circuit branch being in parallel with said supply voltage; and
an evaluating and actuating assembly unit connected to said circuit branch via high ohmic resistors.

* * * * *